United States Patent
Akeson et al.

(10) Patent No.: US 6,267,872 B1
(45) Date of Patent: Jul. 31, 2001

(54) MINIATURE SUPPORT FOR THIN FILMS CONTAINING SINGLE CHANNELS OR NANOPORES AND METHODS FOR USING SAME

(75) Inventors: Mark A. Akeson; David W. Deamer, both of Santa Cruz, CA (US); Daniel Branton, Lexington, MA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/430,240

(22) Filed: Oct. 29, 1999

Related U.S. Application Data

(60) Provisional application No. 60/107,307, filed on Nov. 6, 1998.

(51) Int. Cl.[7] .................................................. G01N 27/26
(52) U.S. Cl. ........................ 205/775; 205/793; 204/450; 204/518; 204/409; 204/600; 204/627; 422/82.01
(58) Field of Search .................................. 204/450, 451, 204/518, 520, 409, 600, 601, 627, 630, 418; 205/775, 792, 793, 789; 422/50, 68.1, 82.01

(56) References Cited

U.S. PATENT DOCUMENTS

| | | | |
|---|---|---|---|
| H201 * | 1/1987 | Yager | 436/151 |
| 4,521,729 | 6/1985 | Kiesewetter et al. | 324/71.1 |
| 5,503,744 | 4/1996 | Ikematsu et al. | 210/257.2 |
| 5,911,871 | 6/1999 | Preiss et al. | 205/775 |

FOREIGN PATENT DOCUMENTS

9425862 * 11/1994 (WO).

OTHER PUBLICATIONS

Brutyan et al. (Mar. 1995), "Horizontal 'Solvent Free' Lipid Bimolecular Membranes with Two–Sided Access can be Formed and Facilitate Ion Channel Reconstitution," *Biochimica et Biophysica Acta*, vol. 1236:339–344.

Kasianowicz et al. (Nov. 1996), "Characterization of Individual Polynucleotide Molecules Using a Membrane Channel," *Proc. Natl. Acad. Sci. USA*, vol. 93:13770–13773.

Wonderlin et al. (Aug. 1990), "Optimizing Planar Lipid Single–Channel Recordings for High Resolution with Rapid Voltage Steps," *Biophys. J. Biophysical Society*, vol. 58:289–297.

* cited by examiner

*Primary Examiner*—T. Tung
*Assistant Examiner*—Alex Noguerola
(74) *Attorney, Agent, or Firm*—Bret E. Field; Bozicevic, Field & Francis

(57) ABSTRACT

Single-channel thin film devices and methods for using the same are provided. The subject devices comprise cis and trans chambers connected by an electrical communication means. At the cis end of the electrical communication means is a horizontal conical aperture sealed with a thin film that includes a single nanopore or channel. The devices further include a means for applying an electric field between the cis and trans chambers. The subject devices find use in applications in which the ionic current through a nanopore or channel is monitored where such applications include the characterization of naturally occurring ion channels, the characterization of polymeric compounds, and the like.

20 Claims, 2 Drawing Sheets

MINIATURE SUPPORT FOR THIN FILMS CONTAINING SINGLE CHANNELS OR NANOPORES AND METHODS FOR USING SAME

CROSS REFERENCE TO RELATED APPLICATIONS

Pursuant to 35 U.S.C. §119 (e), this application claims priority to the filing date of the United States Provisional Patent Application Ser. No. 60/107,307 filed Nov. 6, 1998, the disclosure of which is herein incorporated by reference.

ACKNOWLEDGMENT

This invention was made with Government support under Grant No. HG01360 awarded by the National Institutes of Health. The United States Government has certain rights in this invention.

INTRODUCTION

1. Field of the Invention

The field of this invention is ion channels or nanopores, particularly methods of measuring the ionic current flowing through ion channels or nanopores.

2. Background of the Invention

Methods of measuring the ionic current through a single ion channel are critical to the study of ion channels, which play pivotal roles in a variety of physiological processes. Through such methods, the processes underlying ion permeation and gating have been explored.

One approach for measuring the ionic current flowing through a single ion channel is the patch-clamp technique. In the patch-clamp technique, a small patch of membrane that includes an ion channel of interest is isolated at the tip of a glass micro-electrode. The ion current flowing through the isolated ion channel is then measured. This approach has been invaluable as a research tool, but suffers from limitations in certain circumstances. For example, not all ion channels of interest are accessible by patch-clamp techniques. In addition, patch-clamp techniques do not provide the ability to modulate the membrane component and thus explore the lipid/channel interactions that potentially affect current flow through the channel.

In an alternative approach that can overcome these limitations, the channel of interest is reconstituted in an artificial thin film device. Although several such devices have been developed since the 1960s, there is continued interest in new configurations that reduce capacitance, noise, and solution volume.

Relevant Literature

Of interest are Wonderlin et al., "Optimizing planar lipid bilayer single-channel recordings for high resolution with rapid voltage steps" Biophys. J. (1990) 58:289–297; Brutyan et al., "Horizontal 'solvent-free' lipid bimolecular membranes with two-sided access can be formed and facilitate ion channel reconstitution," Biochimica et Biophysica Acta, (1995) 1236: 339–344; and Kasianowicz, et al., "Characterization of individual polynucleotide molecules using a membrane channel," Proc. Natl. Acad. Sci. USA (1996) 93: 13770–13773.

SUMMARY OF THE INVENTION

Miniature thin film support devices and methods for using the same are provided. In the subject devices, an electrical communication means, e.g. a U tube, connects cis and trans chambers that are filled with an aqueous fluid. At the cis end of the electrical communication means is a conical aperture that is sealed with a thin film into which has been inserted a single nanopore or channel. The subject devices further include a means for applying an electric field between the cis and trans chambers. The subject devices find use in a variety of applications in which the ionic current through the inserted nanopore or channel is monitored or measured for a period of time, e.g. several hours, including the characterization of naturally occurring ion channels, the characterization of polymeric compounds, and the like.

DETAILED DESCRIPTION OF THE INVENTION

Figure 1:
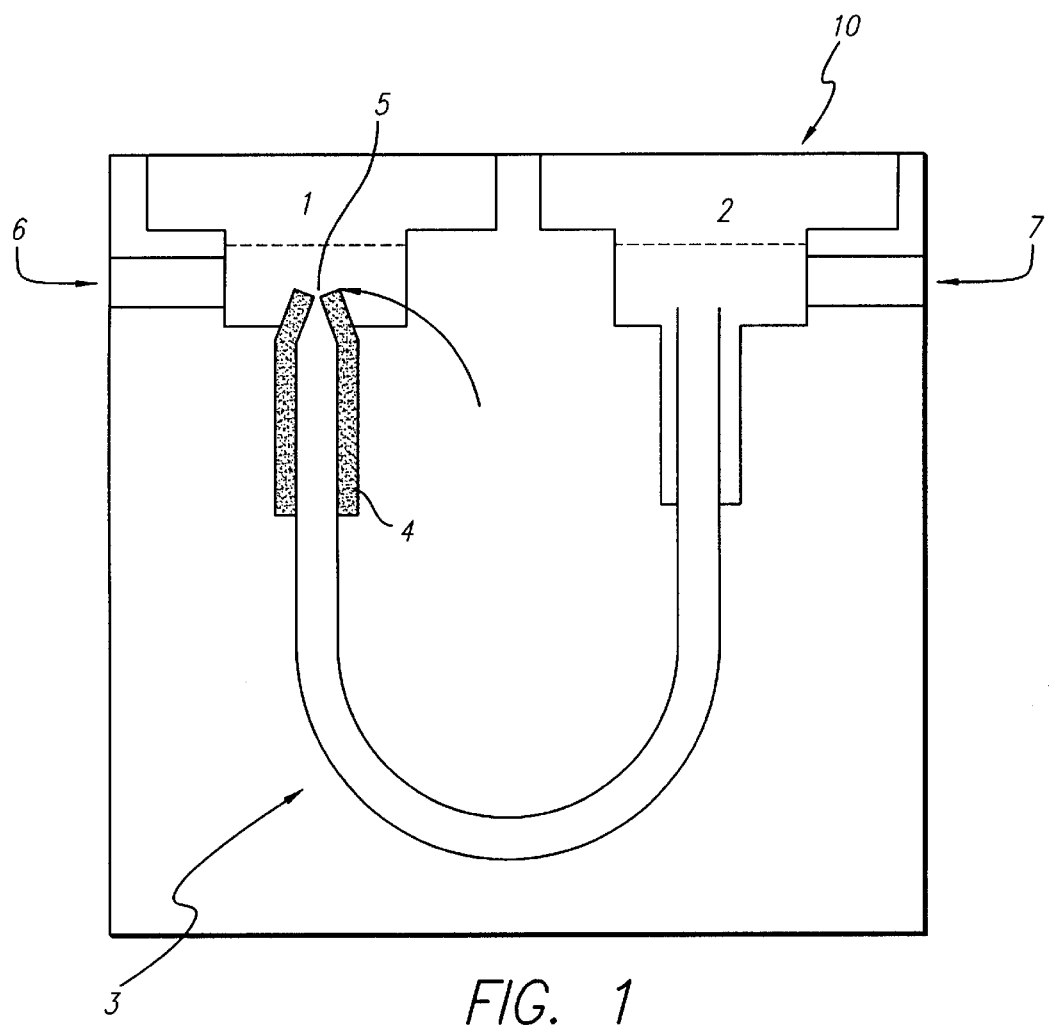
FIG. 1. Horizontal thin film apparatus according to the subject invention. A 0.8 cm inside diameter U-shaped tube connects two 65 $\mu$l baths (A & B) milled into a Teflon support. The baths and the Teflon tube are filled with 1 M KCl buffer. The chamber is connected to an Axopatch 200B amplifier via AgCl electrodes that are pressure fitted into the sides of the two baths. One end of the Teflon U tube has a conical tip that narrows abruptly to a 25 $\mu$m conical aperture. Diphytanoyl PC/hexadecane bilayers are formed across this aperture. α-toxin is inserted into the bilayer following addition of 0.04 $\mu$g to bath A. Nucleic acids are driven through the toxin channel by an applied voltage of 120 mV (+at the trans side (bath B)).

Single-channel thin film devices and methods for their use are provided. The subject devices have a cis chamber connected to a trans chamber via an electrical communication means, e.g. a U-shaped conductor. At the cis end of the electrical communication means is a conical aperture sealed with a thin film having a single nanopore or channel. The subject devices further include a means for applying an electric field between the cis and trans chambers, e.g. cis and trans electrodes. The subject devices find use in a variety of different applications in which the ionic current through a nanopore or channel is monitored. In further describing the subject invention, the subject devices will be described first followed by a review of a number of different representative methods in which the subject devices find use.

Before the subject invention is described further, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

In this specification and the appended claims, the singular forms "a," "an," and "the" include plural reference unless the context clearly dictates otherwise. Unless defined otherwise, all technical and scientific terms used herein have the same meaning as commonly understood to one of ordinary skill in the art to which this invention belongs.

The Subject Devices

As summarized above, the subject single-channel thin film devices include the following elements: (a) a cis chamber; (b) a trans chamber; (c) an electrical communication means connecting the cis and trans chambers; and (d) a thin film at the cis terminus of the electrical communication means that contains a single nanopore or channel.

The cis and trans chambers may have any convenient configuration. As such, the cis and trans chambers may have a conical, cylindrical, cube, or other shape as desired. The volume of the chambers may vary as well, where the volume of each chamber is at least about 1 $\mu$l, usually at least about 10 $\mu$l and more usually at least about 50 $\mu$l, and may be as large as 1 ml or larger, but will usually not exceed about 2 ml and more usually will not exceed about 10 ml. In certain preferred embodiments, e.g. where microgram quantities of nucleic acid are analyzed, as described in greater detail below, the chambers will have relatively small volumes, ranging from about 1 $\mu$l to 10 $\mu$l and usually from about 10 $\mu$l to 50 $\mu$l. The shape and volume of the cis and trans chambers may be the same or different, such that the shape or volume of the cis chamber may be substantially similar to that of the trans chamber or different from that of the trans chamber.

Connecting the cis and trans chambers is an electrical communication means. By electrical communications means is meant a conduit or vessel that is capable of holding a conductor through which an electrical current can flow, e.g. an electrolyte solution. In a typical application, the conduit or vessel has an opening in the cis chamber and the trans chamber, i.e. it has an open cis end and an open trans end, thereby allowing for fluid flow and, importantly, ionic current flow under appropriate conditions, e.g an applied electric field. The conduit or vessel may have a variety of different cross-sectional shapes, where various cross-sectional shapes of interest include circular, square, oval, rectangular, trapezoidal, and the like. In general, the average cross-sectional area along the entire electrical communication means will be at least about 10 $\mu m^2$, usually at least about 50 $\mu m^2$ and more usually at least about 500 $\mu m^2$, where the cross-sectional area may be as large as 2mm$^2$ or larger, but will usually not exceed about 1 mm$^2$ and more usually will not exceed about 0.6 mm$^2$. In preferred embodiments, the electrical communication means is a tubular structure that has a circular cross-sectional shape along its entire length. In these preferred embodiments, the average diameter along the entire length of the electrical communication means is at least about 10 $\mu$m, usually at least about 50 $\mu$m and more usually at least about 500 $\mu$m, where the diameter may be a large as 2 mm or larger, but will generally not exceed about 1 mm and usually will not exceed about 0.8 mm. At least the cis end of the electrical communication means enters the cis chamber through the floor or wall of the cis chamber. The cis end may be flush with the floor or wall of the cis chamber or extend a small distance into the cis chamber, where that distance will not exceed about 2 mm and usually will not exceed about 1 mm. In many embodiments, the trans end will be associated with the trans chamber in an analogous fashion. In such embodiments, the electrical communication means generally is the shape of a "U," e.g. where the electrical communication means is a U-shaped patch tube filled with an electrolyte solution. The length of the electrical communication means typically ranges from about 0.5 mm to 5 mm, usually from about 1 mm to 4 mm and more usually from about 2 mm to 3 mm.

At the cis end of the electrical communication means is a conical aperture (or opening) of $\mu$m dimensions, e.g. a conical fitting or cap with a $\mu$m sized opening. In other words, the cis end of the electrical communication means has an internal conical bore with a hole at the end. As the aperture or opening is of $\mu$m dimensions, it typically has a diameter ranging from about 1 to 100 $\mu$m, usually from about 5 to 50 $\mu$m and more usually from about 10 to 25 $\mu$m. The cis end of the electrical communication means may be fabricated such that it gradually narrows at the cis end to provide for a conical aperture of $\mu$m dimensions (i.e. the conical aperture may be part of the electrical communication means), or the cis end may be capped with a separate conical aperture component or element that fits over or caps the cis end or terminus. In a preferred embodiment, the opening of the conical aperture at the cis end is horizontal, i.e. it is parallel to the water line of fluid, when present, in the cis chamber and the horizon of the substrate on which the device rests.

The horizontal aperture at the cis end of the electrical communication means is sealed with a thin film, such as a lipid bilayer. A variety of different lipid bilayers are known in the art and may be used to produce the thin film and seal the horizontal cis conical aperture. Representative lipid bilayers included those prepared from one or more lipids of the following group: phosphatidlycholine, phosphatidylserine, phosphatidylethanolamine, glycerol mono-oleate, cholesterol, etc. The thin film may also be formed by inorganic materials such as silicon nitride, and the like.

Inserted into the horizontal bilayer is a single channel or nanopore through which ionic current can flow, e.g. from the cis to the trans side of the pore upon application of an applied electric field. As used herein, the terms "nanopore" and "channel" are used interachangeably to refer to structures having a nanoscale passageway through which ionic current can flow. The inner diameter of the nanopore may vary considerably depending on the intended use of the device. Typically, the channel or nanopore will have an inner diameter of at least about 0.5 nm, usually at least about 1 nm and more usually at least about 1.5 nm, where the diameter may be as great as 50 nm or longer, but in many embodiments will not exceed about 10 nm, and usually will not exceed about 2 nm. In those preferred embodiments in which the subject device is designed to characterize polymeric molecules as described in copending application Ser. No. 08/405,735 entitled "Characterization of Individual Polymeric Molecules Based on Monomer Interface Interactions," (UC Reference No. 91-287-2) the inner diameter of the nanopore may be sufficient to allow translocation of singled stranded, but not double stranded, nucleic acids. As such, in these preferred embodiments, the inner-diameter will be at least about 1 nm, usually at least about 1.5 nm and more usually at least about 2 nm, but will not exceed about 3 nm, and more usually will not exceed about 5 nm.

The nanopore should allow a sufficiently large ionic current under an applied electric field to provide for adequate measurement of current fluctuations. As such, under an applied electric field of 120 mV in the presence of pH 7.5 buffered solution (as described in the experimental section, infra), the open (i.e. unobstructed) nanopore should provide for an ionic current that is at least about 1 pA, usually at least about 10 pA and more usually at least about 100 pA. Typically, the ionic current under these conditions will not exceed about 0.5 nA and more usually will not exceed about 1 nA. In addition, the channel should provide for a stable ionic current over a relatively long period of time. Generally, channels finding use in the subject devices provide for accurate measurement of ionic current for at least about 1 min, usually at least about 10 min and more usually at least about 1 hour, where they may provide for a stable current for as long as 24 hours or longer.

The single nanopore that is inserted into the lipid bilayer may be a naturally occurring or synthetic nanopore. Typically the nanopore will be a proteinaceous material, by which is meant that it is made up of one or more, usually a plurality, of different proteins associated with each other to produce a channel having an inner diameter of appropriate dimensions, as described above. Suitable channels or nanopores include porins, gramicidins, and synthetic peptides. Of particular interest is the heptameric nanopore or channel produced from α-hemolysin, particularly α-hemolysin from *Staphylococcus aureus,* where the channel is preferably rectified, by which is meant that the amplitude of the current flowing in one direction through the channel exceeds the amplitude of the current flowing through the channel in the opposite direction.

The single-channel thin films of the device are configured so as to provide for high resistance, low noise and stability. As such, the resistance of the subject single-channel bilayers is at least about 1 gigaohm, usually at least about 10 gigaohm and more usually at least about 200 gigaohm, where the resistance may be as high as 500 gigaohm or higher. The noise preferably does not exceed about 0.6 pA and usually does not exceed about 0.5 pA RMS at 5 kHz bandwidth in whole cell mode, and does not exceed about 0.4 pA and usually does not exceed about 0.2 pA RMS in patch mode. Furthermore, the subject single channel bilayers are stable for period of at least about 1 min, usually at least about 1 hour under an applied electric field of 100 mV or more, where the subject bilayers may be stable for much longer periods under the same conditions, e.g. they may be stable for periods of 24 hours or longer. In addition, the capacitance of the bilayer ranges from about 0.3 to 1.5 $\mu F$ $cm^{-2}$, usually from about 0.4 to 1.2 $\mu F$ $cm^{-2}$ and more usually from about 0.3 to 0.4 $\mu F$ $cm^{-2}$.

The subject devices also generally comprise a means for applying an electric field between the cis and trans chambers, and therefore between the cis and trans sides of the bilayer and single nanopore present therein. The electric field applying means is typically capable of generating a voltage of at least about 10 mV, usually at least about 50 mV and more usually at least about 100 mV. Typically, the electric field generating means is made up of silver chloride electrodes positioned in the cis and trans chambers that are connected to a voltage source.

The device typically further comprises a means for monitoring the current flow through the channel and processing the observed current flow to produce a usable output. Generally, such monitoring means includes a very low noise amplifier and current injector, and an analog to digital (A/D) converter. The device may further comprise other elements of the output generating system, including data acquisition software, an electronic storage medium, etc. A suitable system is described in the experimental section, infra.

The cis and trans chambers may be fabricated from a wide variety of materials. Typically these components will be fabricated or at least lined with a relatively inert material, such as a polymeric material, e.g. Teflon. The components may be fabricated using any convenient technique, e.g. machining.

Preparation of the Subject Devices

The subject devices may be prepared as follows. The cone-shaped bore in the electrical communication means (U tube) is most easily produced by molding heat shrinkable Teflon tubing (Cole-Parmer) around a steel mandril that has been machined into the appropriate shape (e.g. a mandril prepared from an 0.80 mm stainless steel straight rod, with a tip ground to a highly polished 80° point, where the tip is not rounded). After removing the mandril, a microtome is used to cut away excess Teflon from the tip until a hole of the desired size is produced. A typical hole is in the range of 20–40 micrometers. The subject process is further disclosed in FIG. 6 of priority application Ser. No. 60/107,307, the disclosure of which is herein incorporated by reference. The U-tube or electrical communication means is then threaded into a Teflon holder thus connecting the cis and trans chambers, such that the cis end of the electrical communication means is horizontal, e.g. arises from the floor of the cis chamber. In a preferred embodiment, the cis and trans chambers, electrical communication means and conical aperture are assembled to produce a device as shown in FIG. 1. In FIG. 1, device 10 comprises cis chamber or bath 1 and trans chamber or bath 2. Connecting the floors of cis and trans chambers is patch tube 3. At the cis end of the electrical communication means is conical aperture capping element 4 comprising aperture 5 (e.g. 25 $\mu m$ aperture). Also present are electrodes 6 and 7.

Following assembly of the above components, the cis and trans chambers may be cleaned as desired. See the experimental section, infra, for a specific representative cleaning protocol. Following cleaning, the aperture is then typically coated with a lipid solution dissolved in a suitable solvent, typically an organic solvent, where the solvent is then evaporated from the aperture to leave a dry, lipid coated aperture. Next, the cis and trans chambers, as well as the electrical communication means, are filled with an appropriate buffered medium, e.g. a buffered salt solution (such as a 1.0 M KCl solution) at pH ranging from about 5 to 9, usually from about 7 to 8. Electrodes capable of serving as the applied electric field generating means are then placed into the trans and cis chambers. See FIG. 1 in which the electrodes are indicated as elements 6 and 7.

The next step in the fabrication process is to seal the aperture with a thin film. One protocol for sealing the aperture with a lipid bilayer is to paint the lipid bilayer onto the aperture. In painting the lipid bilayer onto the aperture, a bristle of sufficient dimensions, e.g. 10 to 200 $\mu$m diameter, usually 50 to 100 $\mu$m diameter, is dipped into a suitable lipid solution (e.g. lipid in organic solvent, concentration range from about 1 to 5 mg per ml, usually from about 2 to 4 mg per ml). The dipped bristle is then gently brushed against the aperture, which results in the formation of a lipid bilayer that seals the aperture. The seal is then tested and the aperture may be brushed repeatedly with a clean bristle until a bilayer with the desired capacitance is obtained.

The final step in the preparation of the subject device is the insertion of the nanopore into the lipid bilayer. Typically, an aqueous nanopore or channel comprising solution is introduced into the cis chamber and an electric field is applied across the lipid bilayer in a manner sufficient for a single channel to insert or intercalate into the lipid bilayer. The nanopore or channel concentration in the cis bath following introduction of the stock solution (i.e. the solution comprising the nanopore or channel) ranges from about 0.8 ug per ml to 5 ug per ml, usually from about 1 ug per ml to 4 ug per ml and more usually from about 1.2 to 2.5 ug per ml. The voltage applied between the cis and trans sides of the bilayer ranges from about 10 to 200 mV, usually from about 100 to 150 mV.

Following insertion of a single nanopore into the bilayer, the device is ready for use in applications where ionic current through the single channel is monitored.

Uses of the Subject Devices

The subject devices find use in a variety of different applications in which the ionic current through a nanopore or channel is monitored. Representative applications in which the subject devices find use include: (a) the study and characterization or analysis of naturally occurring ion channels or ion permeable passages; and (b) the characterization of polymeric compounds, e.g. the determining of the base sequence of a nucleic acid; and the like.

Where the device is used to characterize the properties of a naturally occurring ion channel, the nanopore that is inserted or present in the lipid bilayer covering the aperture is the ion channel of interest. The ionic current through the ion channel is then measured under various conditions, e.g. in the presence of various buffer solutions, agents, lipid bilayers and the like, so as to characterize the ion channel. For examples, see Wonderlin et al., "Optimizing planar lipid bilayer single-channel recordings for high resolution with rapid voltage steps" Biophys. J. (1990) 58:289–297; and Brutyan et al., "Horizontal 'solvent-free' lipid bimolecular membranes with two-sided access can be formed and facilitate ion channel reconstitution," Biochimica et Biophysica Acta, (1995) 1236: 339–344.

The subject devices also find use in methods of characterizing polymeric molecules, e.g. determining the sequence of bases in a given nucleic acid. In such methods, the polymer is moved relative to the nanopore in a manner such that each different monomeric unit of the polymer causes a correspondingly different current to flow through the nanopore. For example, a single stranded nucleic acid may be translocated through the nanopore and the effect of each base on the current flowing through the nanopore monitored and recorded. From the resultant recorded current fluctuations, the base sequence of the nucleic acid can be determined. Methods of characterizing polymeric molecules in this manner are further described in application Ser. No. 08/405,735 and entitled Characterization of Individual Polymer Molecules Based on Monomer-interface Interactions (UC Ref: 91-287-2), the disclosure of which is herein incorporated by reference.

The following examples are offered by way of illustration and not by way of limitation.

EXPERIMENTAL

I. Preparation of a Horizontal Bilayer Containing a Single Channel Using a Miniature Horizontal Support A single channel was inserted into a bilayer on the horizontal aperture as follows.

A. Formation of diphytatnoyl PC/hexadecane bilayers on a horizontal aperture.

A miniature support was manufactured as described under 'Preparation of Subject Devices', supra. A lipid bilayer was then formed as follows: The aperture and the Teflon bath holding the aperture were first cleaned for 10 min in boiling 5% nitric acid, then rinsed in nanopure water. Just before use, the aperture and bath were rinsed with ethanol followed by hexane, and then air dried. The aperture was then coated with a thin film of diphytanoyl PC (obtained from Avanti Polar Lipids, Birmingham, Ala.) by applying 5 $\mu$l of a 200 $\mu$g per mL solution in spectroscopy grade hexane which was then evaporated with a light stream of air injected through the U-tube from the trans side. The chambers on both sides of the aperture were then filled with 65 $\mu$l of buffer composed of 1.0 M KCl, 5 mM HEPES/KOH at pH 7.5. Silver chloride electrodes using standard methods were placed directly into each bath and were attached to an Axopatch 200B amplifier. To paint a bilayer, a single one-centimeter-long bristle on a 000 brush was dipped into a 3 mg per mL diphytanoyl PC solution in spectroscopy grade hexadecane. The bristle was then gently brushed across the aperture as viewed by a standard dissecting microscope. A 5 mV, 60 cycle square wave was applied across the aperture as a seal test. Once a seal was achieved the aperture was brushed repeatedly with a clean bristle until a capacitance of about 0.6 $\mu$F cm$^{-2}$ was achieved.

B. Insertion of individual $\alpha$-hemolysin channels into the DiphylanoylPC/hexadecane bilayer.

$\alpha$-hemolysin lyophilized in phosphate buffer (Calbiochem, LaJolla, Calif.) was dissolved in nanopure water at 2 $\mu$g per $\mu$l and dispensed as 2 $\mu$l aliquots into 0.2 $\mu$mL polypropylene tubes. These aliquots were frozen at $-20°$ C. On the day of an experiment, a single tube of toxin was placed on ice and diluted in 1.0 M KCl/HEPES buffer to a final concentration of 0.04 $\mu$g per $\mu$l. One $\mu$l of this diluted stock was added to the cis side of the bilayer and mixed gently. Voltage (120 mV tranms positive) was then applied across the bilayer. A single channel typically inserted into the bilayer within 10–60 minutes as indicated by an abrupt increase in current. This long incubation period at low toxin concentration (as opposed to short incubation at high concentration) was preferable because it reduced the frequency of insertion of additional undesired channels during experiments. In the event that no channel insertion was observed in one hour, a second 0.04 $\mu$g aliquot of toxin was added. This generally resulted in a channel within an additional 15 minutes. Upon channel insertion, the cis chamber was immediately perfused with 2 mL of buffer, i.e. About 30 times the bath volume. The single channels intercalated on this first attempt were of two general types: i) a rectifying channel with 116–126 pA current 120 mV trans positive) vs 86 pA current 120 mV trans negative); and ii) a non-rectifying channel with approximately 50 pA current at +/−120 mV. Single rectifying channels were used immediately for nucleic acid analysis. The low amplitude, non-rectifying channels do not translocate nucleic acids (data not shown) and were therefore removed by rupturing the bilayer with a brief 1.3 V DC pulse. The bilayer was then reformed by passing a single bristle across the Teflon aperture using residual diphytanolPC/hexadecane adhering to the Teflon surface. Occasionally, during bilayer reformation, a single rectifying channel of the preferred orientation would insert. If not, the bilayer was ruptured again. This cycle was repeated up to ten times. If no useable channel inserted after ten attempts, toxin 1 $\mu$l of the 0.04 $\mu$g per $\mu$l stock) was re-added and incubated for up to one hour as above.

The resultant bilayers are very high resistance (>200 gigaohm), low noise 0.6 pA RMS at 5 kHz bandwidth in whole cell mode, 0.2 pA RMS in patch mode using an Axopatch 200B amplifier), and are stable for many hours at applied voltages in excess of 150 mV. The devices had the added advantages of low capacitance, small bath volume which permits use of microgram quantities of nucleic acids, and facile observation of the bilayer formation process by conventional light or fluorescence microscopy.

II. Use of the Device

The device described above was used to characterize polymeric molecules as follows:

A. Preparation of Polymeric Molecules

1. Preparation of RNA homopolymers.

Homopolymers of polycytidylic acid and polyadenylic acid 2000+nt) were purchased from Fluka (Ronkonkoma, N.Y.). To generate shorter fragments, stock solutions were hydrolyzed in alkaline buffer by a modification of an earlier technique Briefly, 5 mg of full length RNA homopolymers were weighed into a 12 mL polypropylene tube. To this was added 1 ml of alkaline buffer (pH 10.2, 40 mM NaHCO$_3$, 60 mM Na$_2$CO$_3$) pre-warrned to 60° C. For a product ranging in size from 100 to 500 nt in length, the solution was incubated at 60° C. for 23.5 minutes and the reaction stopped by adding 100 $\mu$l of 3 M sodium acetate, pH 5.2, and 50 $\mu$l of 10% glacial acetic acid. The RNA was precipitated in 2.5 volumes of ethanol at −20° C. The pellet was rinsed in 80% ethanol, then redissolved in 1 volume water and 1 volume 2×formamide loading buffer 90% formamide, 10% 10× MOPS RNA buffer). The product was loaded on an 8% polyacrylamide/MOPS gel and run at 4 volts per cm alongside RNA markers (Century Markers, Ambion Inc., Austin, Tex.). The gel was then examined by UV shadowing and RNA fragments of varying length were excised and eluted from the gel by electrophoresis. The sized RNA was then ethanol-precipitated and redissolved in water or pH 7.5 TE buffer at 2-to-5 $\mu$g per $\mu$l.

2. Synthesis of DNA template for synthesis of A(30)C(70) Gp RNA.

A 134 base DNA oligo-nucleotide composed of the sequence
TAATACGACTCACTATAGGGA(A$_{29}$)/C($_{70}$) GGTACCACACAC (SEQ ID NO:01)
was purchased from Midland Certified Reagents (Midland. Tex.). Full-length 134 nt strands were separated from incomplete strands by electrophoresis on an 8% preparative PAGE/TBE gel at 100 V for 4 hours. The desired band was excised, the full length material was electroeluted from the gel slice, precipitated in ethanol, rinsed twice with 80% ethanol, air-dried, then dissolved in water to give a final concentration of 1 $\mu$g per $\mu$l.

Double-stranded template was synthesized from the purified single-stranded 134mer using Sequenase (Amersham/U.S. Biochemical, Cleveland, Ohio). Briefly, 1 $\mu$g of the 134mer (25 pmol final) were combined with 0.2 $\mu$g of a 14 base reverse complement to the 3' end of the 134mer 50 pmol final), 4 $\mu$l of Sequenase 5× buffer, and 3 $\mu$l nanopure water. This mixture was heated to 65° C. for 2 minutes and gradually cooled to 4° C. over 30 minutes to permit annealing of the reverse complement to the 134 nt strand. This solution was then heated to 37° C. for two minutes and combined with 1 $\mu$l 0.1 M DTT, 2.4 $\mu$l of a 2.5 mM dNTP mixture at room temperature, and 6 $\mu$l of pure water. This solution was brought to 37° C. for 1 minute, combined with 1 $\mu$l of 13U per $\mu$l Sequenase and then incubated at 37° C. for 45 minutes. The resulting double-stranded DNA product was stored at −20° C.

3. In Vitro Synthesis of A(3 0)C(70)Gp RNA.

RNA was synthesized using the 134 nt double-stranded DNA template and a T7 RNA polymerase-based kit designed to give very high yields of short transcripts (Megashortscript, Ambion Inc., Austin, Tex.). Briefly, we combined, in order, at room temperature, 4 $\mu$l nanopure water, 2 $\mu$l 10× transcription buffer, 2 $\mu$l each of 75 mM ATP, CTP, UTP, GTP, 4 $\mu$l of dsDNA template from the previous step, and 2 $\mu$l Megashortscript(T7 RNA polymerase) enzyme stock. This mixture was incubated at 37° C. for 2 hours. At the end of the incubation, 1 $\mu$l of 2U/$\mu$l DNAse 1 was added along with 0.25 $\mu$g of RNAse T1 (Life Technologies) to cleave undesired ends of the RNA product at G residues. This digestion was incubated at 37° C. for 15 minutes. The product was then run on an 8% PAGE gel in 1× MOPS RNA buffer at 80 V. The desired 101 nt band was excised and eluted by electrophoresis. The elution buffer was then exchanged for pH 7.5 TE buffer using a Bio-Rad 30 spin column (Hercules, Calif.). The final product was stored at 2 $\mu$g per $\mu$l in a −20° C. freezer.

B. Current Blockades Produced by Polymeric Molecules

1. Single Channel Clurrent Recordings.

Current readings across single α-hemolysin channels were acquired using an Axopatch 200B integrating patch clamp amplifier (Axon Instruments, Foster City, Calif.) in voltage clamp mode. Unless otherwise noted, data were acquired at 10 $\mu$s intervals in the whole cell configuration and were filtered at 10 kHz using a low-pass bessel filter. The analog signal was digitized using an Axon Instruments Digidata 1200 Series Interface, and then stored using Pclamp 6.02 software (Axon Instruments, Foster City, Calif.). Before the addition of RNA to the cis chamber, data were acquired in gap free format for 15 seconds each at 0, +120 mV, and −120 mV. RNA (10–15 $\mu$g) was added to the cis chamber, and blockades of current were examined at 120 mV (trans positive) for five minutes. Blockades were stored in pClamp 6.02 (Fetchex) using the event driven format for five minutes.

Blockades of ionic current caused by occupancy of the α-hemolysin pore by polyadenylic acid (polyA RNA (200 $\mu$g/ml of 150±50 nt long polyA RNA)) were first measured. The channel had an open current of 117 pA in 1 M KCl buffer at 120 mV potential. The polyA blockades fell into three populations: i) relatively short (<200 μs) blockades that reduced the current by 40–60 pA; ii) blockades of indeterminate length that reduced the channel current by 65 pA to a residual current of about 50 pA (55% blockades); and iii) blockades of 1.5 to 2.5 ms that reduced the channel current by about 98 pA to 19 pA of residual current 84% blockades). The duration of the third class of blockades was strand-length dependent, whereas the duration of the first two classes was length independent. Occasionally, polyA blockades would have a biphasic signature in which an initial 55% blockade would transition to an 84% blockade.

The pattern of blockades caused by polyC was easily distinguishable from the pattern for polyA whether the polymers were examined separately or in combination. That is, the channel current was reduced significantly more by polyC RNA 200 μg/ml of 125±/50 nucleotide long polyC) (typically 95% blockades) than by polyA RNA 84% blockades) and the polyC blockades were shorter in duration, averaging 6 μs per nucleotide compared to 16 μs per nucleotide for polyA. Also, polyC RNA rarely induced lower amplitude blockades or biphasic blockades that were very common with polyA RNA.

Figure 2:
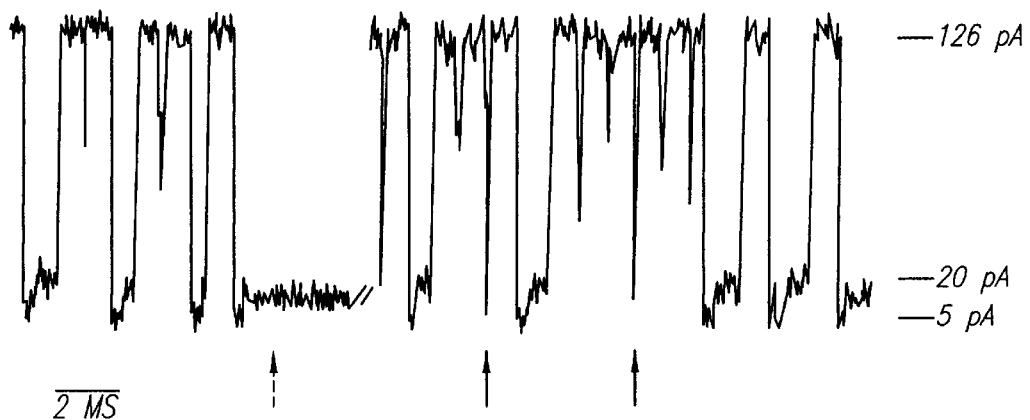
FIG. 2. Typical blockades of monovalent ion current in the α-hemolysin pore caused by A(30)C(70)Gp RNA observed with the device shown in FIG. 1. A single α-hemolysin channel was inserted into the bilayer with an open current of 126 pA at 120 mV in 1 M KCl buffer. Following control measurements in the absence of RNA, A(30)C(70)Gp RNA was added to the civ bath at 100 $\mu$g mL$^{-1}$. Each event represents translocation of a single RNA molecule across the pore. In this experiment, most biphasic events had the orientation 5 pA residual current (95 percent current blockade) first followed by a 19 pA residual current 84 percent blockade). This corresponds to the polyC segment at the 3' end of the molecule entering the pore first. The opposite orientation (insert) constituted less than 10% of the blockade events. The solid arrows highlight monophasic current blockades of approximately 95% and 84%; the dashed arrow highlights a permablock that required a voltage reversal to be cleared. This experiment is representative of four experiments with A(30)C(70)Gp RNA in which successful preparative cutting of the T7 RNA polymerase product by T1 RNase was confirmed by PAGE.

This suggested that a transition from polyA to polyC segments within individual RNA molecules should be detectable by the α-hemolysin pore. To test this prediction, in vitro transcription and ribonuclease T1 digestion was used to generate a 101-nucleotide-long RNA of the nominal composition A(30)C(70)Gp. Typical biphasic blockades caused by occupancy of the channel by this RNA are shown in FIG. 2. As predicted, one component of the blockade reduced the channel current by 95% (consistent with polyC RNA), and the other component reduced the current by 84% (consistent with polyA RNA). Monophasic blockades of each characteristic amplitude were also abundant (solid arrows in FIG. 2), as were permanent blockades that required reversal of the membrane potential to be cleared (dashed arrow, FIG. 2).

That the biphasic signatures in FIG. 2 were due to the C-to-A transition in A(30)C(70)Gp and that they could not be due to the polyA segment alone was established as follows. Blockades caused by A(30)C(70)Gp were measured before and after addition of ribonuclease A. Ribonuclease A cleaves single-stranded RNA on the 3' end of pyrimidine residues (Davis, L. G., W. M. Kuehl, J. F. Battey. 1994. Basic Methods in Molecular Biology, 2nd Edition. Appleton and Lange, Norwalk, Conn.) and would, therefore, rapidly convert A(30)C(70)Gp to a mixture of A(30)Cp with very short polyC oligomers and CMP. FIG. 3a shows results from this experiment, confirming an abrupt decrease in the frequency of biphasic 95%-to-84% blockades in the presence of ribonuclease A. Thus, the biphasic signatures shown are caused by translocation of the intact A(30)C(70)Gp strand and they cannot be accounted for by anomalous amplitude transitions in polyA RNA alone. This experiment also revealed that the frequency of monophasic 95% blockades was significantly reduced (FIG. 3b), while the frequency of 84% blockades approximately doubled over the twenty minute incubation period (FIG. 3c), consistent with generation of an RNA population dominated by polyA strands.

Figure 3:
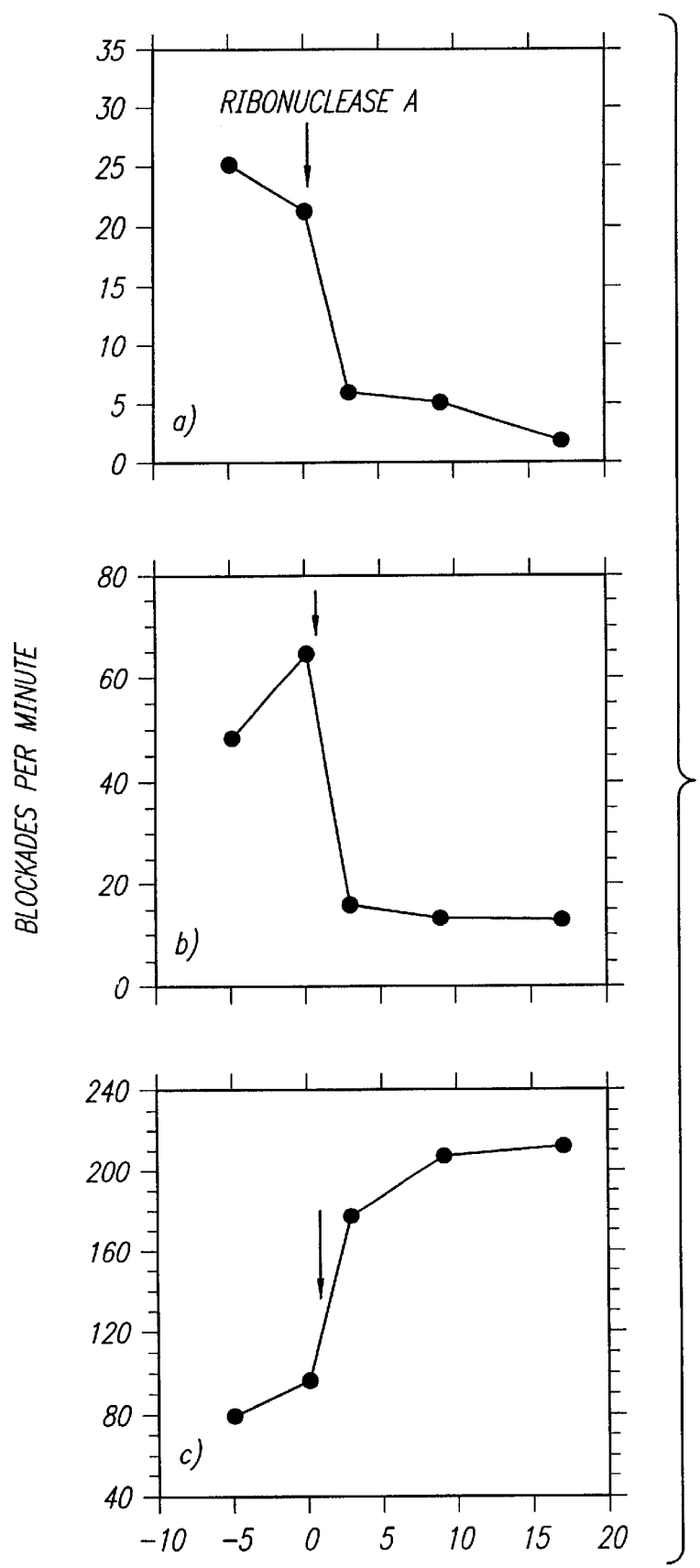
FIG. 3. Effect of ribonuclease A addition upon the frequency of biphasic blockades caused by A(30)C(70)Gp RNA observed in the device of FIG. 1. A single α-hemolysin channel was inserted into the bilayer with an open current of 125 pA at 120 mV in 1 M KCl buffer at room temperature. Following control measurements in the absence of RNA, A(30)C(70)Gp RNA was added to the cis bath for a final concentration of 100 $\mu$g mL$^{-1}$. Channel blockades were recorded for ten minutes, and then ribonuclease A (20 $\mu$g mL$^{-1}$) was added to the cis bath. Blockades were then acquired in two minute increments at intervals up to 20 minutes. a) Frequency of 95%-to-84% biphasic blocks similar to those shown in FIG. 2. b) Frequency of monophasic blockades that reduce the channel current by 95% as observed in experiments with polyC alone. c) Frequency of monophasic blockades that reduce the channel current by 84 percent as observed with polyA alone. In all cases, events were counted if the specified blockade amplitude was achieved for a minimum of 50 $\mu$s.

The results demonstrate that segments of polyA and polyC in individual RNA molecules can be read during translocation of single molecules through a nanometer-scale pore using the device according to the subject invention. This conclusion is based on the following evidence: i) RNA homopolymers of polyA and polyC cause measurably different blockades of current in the α-hemolysin channel. Importantly, this difference includes the largest amplitude blockades (84% blockade for polyA vs 95% blockade for polyC) whose duration is strand-length dependent—a requirement of vectorial transport. ii) When segments of polyA and polyC are linked together in individual RNA molecules, biphasic blockades are observed that transition from a 95% current reduction to an 84% current reduction (FIG. 2) in a manner that is quantitatively consistent with the homopolymer experiments. The frequency of this biphasic signature is greatly reduced in the expected manner following cleavage of A(30)C(70)Gp by ribonuclease A (FIG. 3).

The above results show that the subject devices can be used to distinguish between short segments of polycytidylic acid and polyadenylic acid within individual RNA strands.

It is evident from the above results and discussion that improved single-channel thin film devices are provided by the subject invention. One novel feature of the device is the conical bore, which can be molded in a partition composed of inexpensive heat shrinkable material, such as Teflon tubing. This aspect of the invention allows the device to be produced in large numbers as a disposable item for manufacture. In addition, the conical angle of the hole contributes to the stability of the film in the device. A second novel feature is the small size and insulating properties of the support which lead to extremely low electrical noise in the output signal. The small size also allows very small volumes of solution to be used during the measurement. Thus, the subject devices combine the advantages of a conical aperture with the advantages of horizontal bilayers to yield devices having high resistance, low noise and high stability. In addition, the subject devices have the advantages of low capacitance and can be used to analyze microgram quantities of nucleic acid. A third novel feature is the U-tube electrical means which allows the user to produce a horizontal film accessible to microscopic examination. As such, the bilayer formation process is readily observable in the subject devices using conventional light or fluorescence microscopy.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A single-channel thin film device comprising:
   a cis chamber;
   a trans chamber;
   an electrical communication means for holding a conductor of electrical current connecting said cis and trans chambers and having a cis terminus and a trans terminus; and
   a thin-film comprising a single channel, said thin-film covering an aperture at said cis terminus.

2. The device according to claim 1, wherein said single-channel thin-film covered aperture comprises:
   a conical aperture; and
   wherein said single channel is a single nanopore.

3. The device according to claim 2, wherein said nanopore is selected from the group consisting of a naturally occurring proteinaceous channel and a synthetic pore.

4. The device according to claim 1, wherein said device further comprises a means for applying an electric field between said cis and trans chambers.

5. The device according to claim 1, wherein said electrical communication means is a U-shaped tube connecting said cis chamber with said trans chamber.

6. In a method of monitoring a current through a nanopore, the improvement comprising the steps of:
   applying an electrical field between the cis and trans chambers of a single-channel thin film device according to claim 1; and
   monitoring said current,
   measuring the ionic current through said nanopore.

7. The method according to claim 6, wherein said method is a method of characterizing a naturally occurring ion channel.

8. The method according to claim 6, wherein said method is a method of characterizing a polymeric compound.

9. The method according to claim 8, wherein said method of characterizing is a method of sequencing a nucleic acid.

10. The device of claim 1, wherein said conductor is an electrolyte solution.

11. A single-channel thin film device comprising:
    a cis chamber;
    a trans chamber;
    a U-shaped tube connecting said cis chamber with said trans chamber and having a cis terminus and a trans terminus;
    a conical aperture at said cis terminus, wherein said aperture is covered with a thin film comprising a single nanopore; and
    a means for applying an electric field between said cis and trans chambers.

12. The device according to claim 11, wherein said conical aperture has an inner diameter ranging from about 1 to 50 $\mu$m.

13. The device according to claim 11, wherein said nanopore has an inner diameter ranging from about 1 to 10 nm.

14. The device according to claim 13, wherein said nanopore is selected from the group consisting of a naturally occurring protein channel and a synthetic pore.

15. The device according to claim 14, wherein said naturally occurring protein channel is a heptameric channel of α-hemolysin.

16. The device according to claim 15, wherein said channel is a rectifying channel.

17. A method of monitoring ionic current through a nanopore, said method comprising:
    applying an electrical field between the cis and trans chambers of a device according to claim 11; and
    measuring the ionic current through said nanopore.

18. A single-channel thin film device comprising:
    a cis chamber;
    a trans chamber;
    a U-shaped tube connecting said cis chamber with said trans chamber and having a cis terminus and a trans terminus;
    a conical aperture at said cis terminus, wherein said conical aperture has an inner diameter ranging from about 1 to 50 $\mu$m and is covered with a lipid bilayer comprising a single rectifying heptameric channel of α-hemolysin; and
    a means for applying an electric field between said cis and trans chambers.

19. The device according to claim 18, wherein said conical aperture is fabricated from Teflon.

20. The device according to claim 18, wherein said means for applying an electric field comprises a cis electrode and a trans electrode.

* * * * *

SEQUENCE LISTING

<160> NUMBER OF SEQ ID NOS: 1

<210> SEQ ID NO 1
<211> LENGTH: 132
<212> TYPE: DNA
<213> ORGANISM: Artificial Sequence
<220> FEATURE:
<223> OTHER INFORMATION: synthetic polynucleotide

<400> SEQUENCE: 1
taatacgact cactataggg aaaaaaaaaa aaaaaaaaaa aaaaaaaaaa cccccccccc        60
cccccccccc cccccccccc cccccccccc cccccccccc cccccccccc cccccccccc      120
ggtaccacac ac                                                           132